(12) United States Patent
Katz et al.

(10) Patent No.: US 6,316,247 B1
(45) Date of Patent: Nov. 13, 2001

(54) SYSTEM AND METHOD FOR REFINING LIPOSUCTIONED ADIPOSE TISSUE

(75) Inventors: Adam J. Katz; Ramon Llull; J. William Futrell, all of Pittsburgh, PA (US); Marc H. Hedrick, Encino, CA (US); Frank R. Walters, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/333,532

(22) Filed: Jun. 15, 1999

(51) Int. Cl.[7] .................................................. C07G 17/00
(52) U.S. Cl. ........................ 435/267; 435/325; 435/371; 435/271; 435/297.1; 435/304.1; 435/308.1; 210/446; 210/772
(58) Field of Search ..................... 435/325, 370, 435/267, 271, 297.1, 304.1, 308.1; 494/36; 210/632, 446, 448, 768, 772

(56) References Cited

U.S. PATENT DOCUMENTS

| | | |
|---|---|---|
| 5,372,945 | 12/1994 | Alchas et al. . |
| 5,409,833 | 4/1995 | Hu et al. . |
| 5,586,732 | 12/1996 | Yamauchi et al. . |
| 5,786,207 * | 7/1998 | Katz et al. ............................ 435/267 |
| 5,968,356 * | 10/1999 | Morsiani et al. ..................... 210/335 |

* cited by examiner

*Primary Examiner*—David A. Redding
(74) *Attorney, Agent, or Firm*—Debra M. Parrish

(57) ABSTRACT

A device and method for producing refined adipose tissue for use in autologous adipose transplantation or research wherein a sterile environment is maintained. More particularly, a system for refining tissue comprising a first flexible container, a second flexible container having a plurality of pores providing for fluid communication between the interior of the first flexible container and the interior of the first enveloping flexible container, a first port that provides communication between the exterior environment and the interior of the first flexible container and thereby provides a means for introducing fluids into the interior of the first flexible container and allowing waste effluent to exit the first container, a second flexible container, a second port for inserting tissue into the second container and expressing refined tissue out of the container, and a means for controlling the opening and closing of the first and second ports. The method comprises introducing a tissue sample into the system and subjecting it to a washing phase wherein the tissue is agitated, the waste effluent is allowed to exit the system through the first port, and the refined tissue is expressed out the second port for further refinement or transplantation.

13 Claims, 2 Drawing Sheets

SYSTEM AND METHOD FOR REFINING LIPOSUCTIONED ADIPOSE TISSUE

FIELD OF THE INVENTION

The present invention relates to a method and system for refining tissue. In particular, the present invention relates to a method and system for separation, washing and refinement of adipose tissue from liposuctioned effluent.

BACKGROUND OF THE INVENTION

Autologous adipose tissue transplantation is performed by many surgeons for various cosmetic and reconstructive procedures, particularly those relating to the face, hands and other areas. Public confidence in and comfort with synthetic materials (e.g., silicone and teflon) and foreign tissues (e.g., bovine collagen) has declined. Conversely, the interest in and demand for autologous adipose tissue transplantation has risen.

Autologous fat transplantation involves the procurement of adipose tissue by liposuction techniques from an area of abundance, and re-injection of the harvested adipose tissue into a different site of the same individual for cosmetic/reconstructive augmentation or enhancement purposes. Generally, adipose tissue must be as 'clean' or refined as possible before re-introduction to maximize the chances of graft survival. Such refinement preferably is done with as little exposure of the tissue to air as possible (i.e., "anaerobic tissue handling").

Unfortunately, the nature of liposuction procedures preclude easy tissue isolation after initial harvest (especially on a large scale) because the volume and/or viscosity of 'raw' liposuction effluent also contains unwanted components, e.g., oil, blood and anesthetic solution. Currently, there are no standard techniques, methods, or devices that exist for the simple, large scale isolation and refinement of liposuction-harvested adipose tissue. Although patented cannulas, needles and methods for tissue harvest and preparation exist, these techniques are tedious, inefficient and require a pseudo-sterile centrifugation step.

Several devices exist for the isolation of certain cells. For example, U.S. Pat. Nos. 5,035,708 and 5,372,945, issued to Alchas et al., describe an endothelial cell procurement and deposition kit and a device and method for collecting and processing fat tissue and procuring microvessel endothelial cells to produce endothelial cell products. Further, U.S. Pat. No. 5,409,833, issued to Hu et al., discloses a microvessel cell isolation apparatus, U.S. Pat. No. 5,330,914, issued to Uhlen et al., discloses a method for extrapolating extrachromosomal DNA, and U.S. Pat. No. 5,610,074, issued to Beritashvili et al., discloses a centrifuge for separating multiple substances from a mixture. Finally, U.S. Pat. No. 5,786,207, issued to Katz et al., discloses a device for separating adipose tissue.

The present invention, however, is superior to existing inventions. It offers a simpler design, material and manufacturing methodology. Further, none of the devices disclosed above addresses the special concerns presented by working with adipose tissue and preparing it for immediate autologous adipose tissue transplantation, explant culture endeavors or cell dissociations. Thus, although various techniques and devices for cell separation are well documented in the literature, a need exists for a device and method that is more expeditious, efficacious, accessible and practical than current devices and methods.

SUMMARY OF THE INVENTION

The present invention consists of two containers. The first container is a flexible container that houses a second flexible container. The outer flexible container is non-porous and water-tight but the inner flexible container is porous. At the top of the device is at least one "tissue inlet" port that is contiguous with the inner flexible container and has a means for sealing it off from the outside environment. The tissue inlet port enables the introduction of liposuction material and possibly solutions into the inner flexible container. At another section of the device is at least one outlet port that is contiguous with only the outer flexible container and has means for sealing the outlet port that allows for quick and easy efflux of waste.

A description of the method for separating adipose tissue for autologous tissue transplantation is as follows. Liposuctioned tissue removed from the patient is transferred into the device through the inlet port that is contiguous with the inner flexible porous container. Pieces of adipose tissue are "trapped" within the inner flexible container whereas waste components (free oil, blood, serum) are able to drain through the pores and out the outlet port. After all the desired liposuction effluent is transferred, the trapped tissue may be rinsed thoroughly with saline or buffer. For very thorough cleansing, the outlet port is sealed, buffer is added, and the inlet port is sealed. The device is agitated to encourage thorough rinsing of the tissue. Next, the device is held upright and the bottom outlet port unsealed to allow for drainage of waste or active suction of the effluent. This step can be repeated several times as necessary to achieve tissue that is highly "purified". Finally, the washed tissue can be expressed from the inner flexible container by 'rolling' the tissue out through the inlet port (from bottom to top) into receptacles, e.g., syringes, for re-implantation or any other desired receptacle for further preparation before injection. Alternatively, a receptacle can be attached directly to the port such that the tissue can be anaerobically re-injected into the body.

In addition to the immediate clinical application, this present invention maintains the ability to support enzymatic dissociation of adipose tissue into its cellular components for use by individuals engaged in cell-based science, developmental biology, tissue engineering research and genetic engineering.

It is an object of this invention to provide a more efficient, versatile, cost-effective, sterile method and system for refining adipose tissue samples for immediate transplantation.

It is an object of this invention to provide a disposable device for the refinement of adipose tissue.

It is also an object of this invention to provide a more efficient, cost-effective, sterile method and system that overcomes the deficiencies of prior devices and systems for the refinement of adipose tissue for autologous adipose transplantation.

It is an object of this invention to allow a surgeon who is performing liposuction to harvest tissue for autologous adipose transplantation to rapidly, easily, efficiently and sterilely isolate adipose tissue from the other unwanted waste components that are associated with primary liposuction effluent.

Other objects and advantages of the present invention will become apparent from perusing the following detailed description of presently preferred embodiments taken in conjunction with the accompanying drawings.

DETAILED DESCRIPTION OF PRESENTLY PREFERRED EMBODIMENTS

Figure 1:
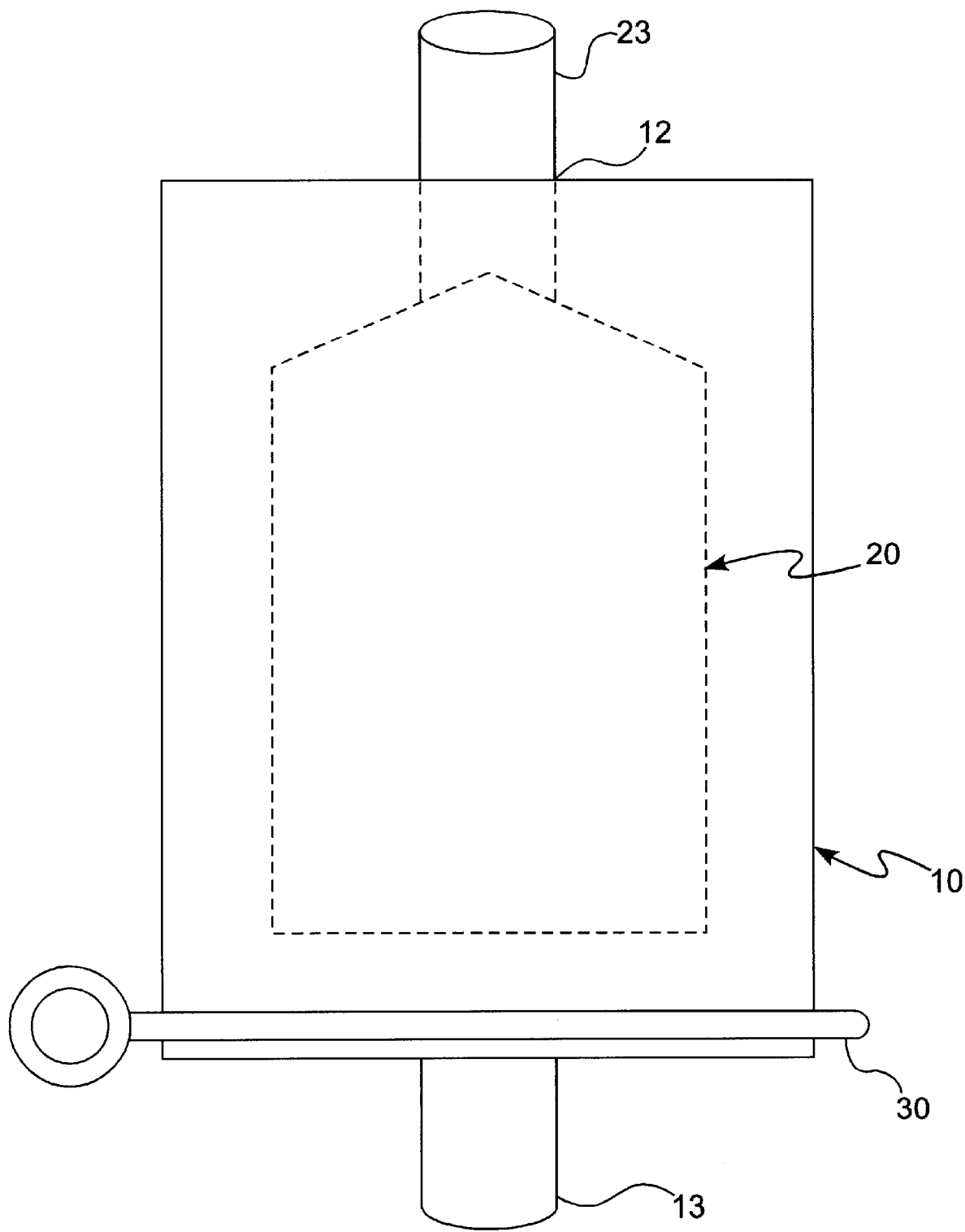
FIG. 1 is a cross-sectional front view of a system embodying this invention.
Figure 2:
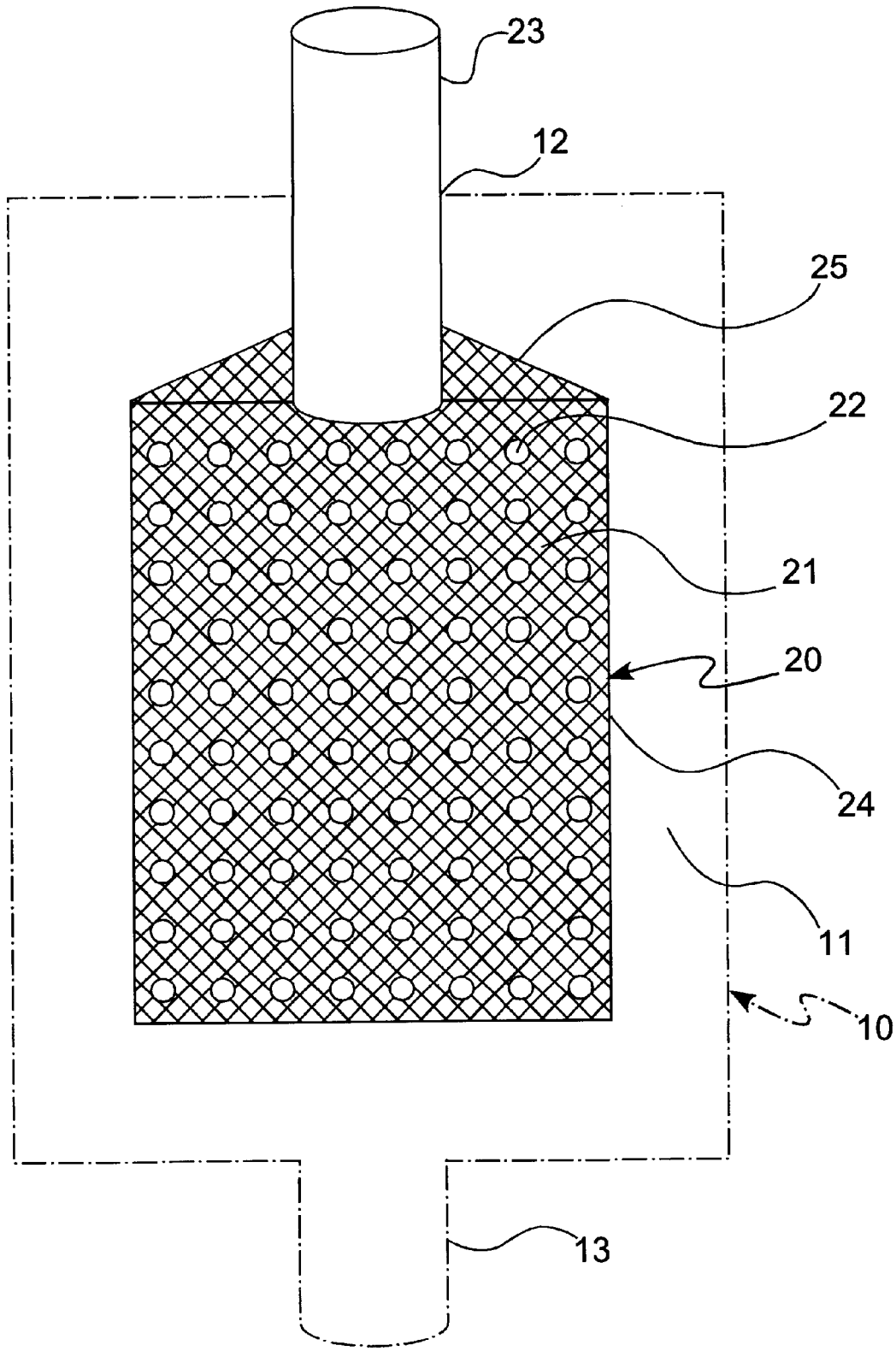
FIG. 2 is a cross-sectional front view of a preferred embodiment of the present invention.

The device is comprised of two containers. Preferably, such containers are flexible. The first container 10, completely envelops the second container 20. In one preferred embodiment the first container and the second container are bags. The first container provides for the containment of washing, rinsing and possibly other solutions and effluent released from the interior of the second container. In a yet more preferred embodiment, the first container is constructed of a translucent material that permits visual observation of processes occurring in the first container. The first container has at least one aperture 12 through which passes at least one port 23 that extends from the environment and into the interior of the second container 21. The apertures in the first container have an airtight and watertight seal along the seams of these ports into the second container.

At least one port 13 (hereinafter collectively referred to as the "first port") also provides for communication between the interior of the first container 11 and the external environment and thereby provides a means for inserting various fluids, e.g., washing and rinsing fluids, and removing such fluids and effluent from the first container. Such first port 13 is capable of being sealed. Even more preferably, such first port is capable of being manually sealed with a clamp. Further, it is preferable that when the first container is held upright, the first port is positioned inferiorly on the first container such that fluids and effluent will egress from the first container with the assistance of gravitational forces, suction or pressure.

As discussed above at least one port 23 (hereinafter collectively known as the "second port") exists which provides a means of communication between the interior of the second container 21 and external environment and which passes through apertures in the first container 12. Such second port is capable of being sealed. Even more preferably, such second port is capable of being sealed manually with a clamp. In an even more preferred embodiment, the second port is capable of interconnecting with a syringe or catheter used to suction the adipose material from the source body such that the adipose tissue is directly transported into the second container anaerobically. Similarly, a cannula or syringe can be attached to the second port for anaerobic transplantation of the refined tissue.

The second container 20, which may be permanently secured in the first container, has a plurality of pores 22 allowing fluid communication between the interior of the second container 21 and the interior of the first container 11. The pores enable fluids inserted in the first container to diffuse from inside the first container into the interior of the second container and interact with tissue(s) which have been inserted therein. Preferably, such pores 22 are located on a substantial area of the surface of the second container 24. The pores of the second container of the present invention are chosen for their optimal pore size for washing and refining a given tissue specimen although preferably such pore size is in the range of approximately 50–2000 micrometers in diameter. Even more preferably, the second container 20 is a mesh material that prevents or minimizes the adhesion of mammalian cells, e.g., nylon mesh.

The internal volume of the second container depends on the size of the tissue specimen to be processed. The second container is secured in the first container while the containers are agitated. Preferably, the second container is positioned within the first container so as to most efficiently consume the interior of the first container and interact with the fluids in the first container. Even more preferably, the second container assumes a shape which facilitates movement of the tissue in the second container and reduces its entrapment therein. In one preferred embodiment, the portion of the second container immediately conjoining the second port is bevelled 25. At the apex of such bevelled portion is the second port 23. In another preferred embodiment, the second container is capable of being rotated within the first container such that centrifugal forces can be used to expel effluent and waste products from the interior of the second container to the interior of the first container.

At the start of the procedure, the first port is sealed and liposuctioned tissue is introduced into the system through the second port 23 providing communication between the external environment and the interior of the second container 23. A washing/rinsing solution is introduced into the first container, either through ports providing access to the interior of the first or second containers 13, 23. If the washing/rinsing solution is introduced through the port providing access to the first container 13, the solution exudes through the pores 22 of the second container to make contact with the tissue in the second container. Preferably, sufficient washing solution is introduced into the system such that the second container, and the tissue therein, is substantially submerged during this washing phase. During the washing phase, the second container is mechanically or, preferably, manually rotated or, preferably, agitated by an external means to facilitate and expedite washing and refinement of the tissue in the second container. After the tissue is thoroughly washed, as determined by macroscopic examination or a pre-established time interval, the first port is opened and, under gravitational forces, the effluent, often treated as waste, is thereby permitted to pass through the first port and into the environment. The washing phase can be repeated to ensure greater purity and refinement of the liposuctioned material.

In another preferred embodiment, the first port is not sealed at the start of the procedure. The tissue is introduced into the inner flexible container via the second port and the waste components (free oil, blood, serum) drain through the pores of the second container, into the first container and out the first outlet port. After all the desired liposuction effluent has drained, rinsing solution is introduced into the system through the second port. The solution washes over the tissue in the second chamber and flows out the first port into the environment.

After the washing phase, the second port is opened and pressure is applied to the first container which transmits pressure to the second container which transmits pressure to the refined tissue therein and compels the tissue to extrude out of the second container through the second port. In one embodiment, the system further comprises a means to facilitate the application of consistent pressure and efficient removal of refined tissue. In one version of this embodiment, a pin 30 is applied at a point on the first container furthest away from the aperture at which the second port extends, and the pin is rolled towards the second port to evenly express the refined liposuctioned material out of the second chamber and into a receptacle, e.g., a syringe, for re-implantation or any other desired receptacle for further preparation before injection. In one preferred embodiment, a receptacle is attached to the second port and the liposuctioned material is anaerobically extruded into the receptacle for immediate use.

It will be obvious to one skilled in the art that it is possible to combine different features of the different embodiments described above to practice the present invention.

What is claimed is:

1. A system for refining adipose tissue comprising:
   a. a first flexible container wherein said first container is airtight and watertight;
   b. a second flexible container wherein said second container is enveloped by said first container and said second container has a plurality of fluid communicating means between the interior of said second container and the interior of said first container;
   c. at least one first port that provides communication between the exterior environment and the interior of said first container and thereby provides a means for introducing solutions into the interior of said first container and removing waste from said first container;
   d. at least one second port that provides communication between the exterior environment and the interior of said second container and thereby provides a means for introducing tissue samples into said second container and extruding refined liposuctioned material out of said second container; and
   e. a means for controlling the opening and closing of said first and second ports.

2. A system for refining tissue according to claim 1 further comprising:
   a. a means for engaging said first container at the point furthest away from said second port and advancing such means towards said second port such that pressure is evenly applied and refined tissue is extruded out of said second port.

3. A system for refining tissue according to claims 1 or 2 wherein said second port has a means of engaging the receptacle used to harvest liposuctioned tissue or/and the receptacle for re-implanting refined liposuctioned tissue.

4. A system for refining tissue according to claims 1 or 2 wherein said second container is bevelled such that at the apex of said bevelled portion is said second port.

5. A system for refining tissue according to claims 1 or 2 wherein said second container is a mesh bag and said pores of said second container are between 50 and 2000 microns.

6. A system for refining tissue according to claims 1 or 2 wherein said means for controlling the opening and closing of said ports consists of applying a clamp manually around said second and first ports.

7. A system for refining tissue according to claims 1 or 2 wherein said first and second containers are bags.

8. A system for refining tissue according to claims 1 or 2 wherein said second container is capable of being rotated within said first container and thereby expel waste from the interior of said second container into the interior of said first container.

9. A method for refining tissue comprising:
   a. providing a system for refining tissue having a first flexible container and a second flexible container enveloped by said first container, said second container having pores providing for fluid communication between the interior of said second container and the interior of said first container, a first port that provides communication between the exterior environment and said interior of said first container and provides a means for introducing solutions into said interior of said first container and allowing the egress of solutions and effluent, a second port for introducing tissue into said second container, said second container having a means for engaging a rotating or agitating mechanism, a means for sealing said first and second ports;
   b. inserting tissue into said second container via said second port;
   c. inserting a washing solution into said first container via said first or second port;
   d. sealing said second port;
   e. permitting said washing solution to exude through said pores providing for fluid communication between said interior of said second container and said interior of said first container and interacting with the tissue inserted therein;
   f. agitating said first and second containers;
   g. allowing effluent to drain through said first port into the environment; and
   h. opening said second port and applying pressure to said first container, said second container, and the tissue in said second container such that refined tissue is expressed out of said system through said second port.

10. A method for refining tissue according to claim 9 wherein said washing solution is introduced into the system under pressure such that the pressure of said washing solution when it interacts with said second container dislodges materials occluding said pores of said second container.

11. A method for refining tissue according to claim 9 further comprising:
   a. sealing said first port before introducing washing and rinsing solution into said system; and
   b. opening said first port after agitating said first and second containers such that effluent exits said first container into the environment.

12. A method for refining tissue according to claim 9 further comprising:
   a. attaching a receptacle to said system and anaerobically expressing the tissue into said receptacle for re-implantation.

13. A method for refining tissue according to claim 9 wherein said agitation of said second container is rotation of said second container within said first container such that centrifugal forces expel waste from the interior of said second container into the interior of said first container.

* * * * *